(12) United States Patent
Esrock (10) Patent No.: US 6,319,001 B1
(45) Date of Patent: Nov. 20, 2001

(54) FITTING FOR DENTAL SYRINGE TIP

(76) Inventor: Bernard S. Esrock, 320 Dungate Dr., Chesterfield, MO (US) 63017

( * ) Notice: Subject to any disclaimer, the term of this patent is extended or adjusted under 35 U.S.C. 154(b) by 0 days.

(21) Appl. No.: 09/262,759

(22) Filed: Mar. 4, 1999

Related U.S. Application Data (63) Continuation of application No. 08/787,243, filed on Jan. 24, 1997, now Pat. No. 5,927,975.

(51) Int. Cl.$^7$ .................................................. A61G 17/02
(52) U.S. Cl. ............................................................ 433/80
(58) Field of Search .............................. 433/80, 82, 126; 604/283; 285/133.1, 322, 382

(56) References Cited

U.S. PATENT DOCUMENTS

| | | |
|---|---|---|
| D. 352,354 | 11/1994 | Davis et al. . |
| 1,683,350 | 9/1928 | Hein . |
| 1,802,499 | 4/1931 | Chapman . |
| 2,371,971 | 3/1945 | Main et al. . |
| 2,452,275 | 10/1948 | Woodling . |
| 2,561,827 | 7/1951 | Soos . |
| 2,833,567 | 5/1958 | Bacher et al. . |
| 2,873,985 | 2/1959 | Baldwin . |
| 2,978,262 | 4/1961 | Franck . |
| 3,140,106 | 7/1964 | Thomas et al. . |
| 3,184,706 | 5/1965 | Atkins . |
| 3,254,646 | 6/1966 | Staunt et al. . |
| 3,287,033 | 11/1966 | Currie . |
| 3,361,449 | 1/1968 | Parro . |
| 3,361,460 | 1/1968 | Jansen . |
| 3,394,954 | 7/1968 | Sarns . |
| 3,423,109 | 1/1969 | New et al. . |
| 3,454,290 | 7/1969 | Tairraz . |

(List continued on next page.)

FOREIGN PATENT DOCUMENTS

| | | |
|---|---|---|
| 2 213 732 | 8/1989 | (GB) . |
| WO 92/14434 | 9/1992 | (WO) . |
| WO 92/14498 | 9/1992 | (WO) . |

OTHER PUBLICATIONS

Legris, Inc., "Quick Reference Product Guide," pp. 1–6, admitted prior art.
"Push–Connect," Weatherhead, pp. 1, admitted prior art.
"Cartridge Fittings," Norgren, Apr. 1996, pp. 1–2.

Primary Examiner—Ralph A. Lewis
(74) Attorney, Agent, or Firm—Senniger, Powers, Leavitt & Roedel (57) ABSTRACT

A fitting for releasably and sealingly connecting a conduit to a medical instrument. The fitting comprises a body having a proximal end, a distal end and a longitudinal axis extending between the ends. The body has a recess extending on the axis, a bottom adjacent its proximal end and is open at its distal end. The bottom of the body includes first and second passages for flow of first and second fluids. The fitting further includes a quick-connect device mounted in the recess and having a gripping mechanism. The conduit is receivable in the gripping mechanism for movement of the conduit in proximal and distal directions with respect to the body. The gripping mechanism permits one end of the conduit to be pushed through an opening of the quick-connect device to a position in which a tubular connector provides a sealing connection between a central passageway in the conduit and the first passage in the bottom of the body. The gripping mechanism is operable to apply a progressively increasing gripping force to the conduit as the conduit moves away from the bottom until the conduit reaches a position in which the gripping force prevents substantial further movement of the conduit away from the bottom. The fitting further includes a manually operable device for moving the gripping mechanism in a proximal direction relative to the body to cause the gripping mechanism to move radially outward to release the conduit so it can be removed from the body.

9 Claims, 8 Drawing Sheets

U.S. PATENT DOCUMENTS

| | | |
|---|---|---|
| 3,479,058 | 11/1969 | Chandler . |
| 3,540,760 | 11/1970 | Miller et al. . |
| 3,563,575 | 2/1971 | Sandford . |
| 3,570,483 | 3/1971 | Stram . |
| 3,606,396 | 9/1971 | Prosdocimo et al. . |
| 3,624,812 | 11/1971 | Rosan et al. . |
| 3,653,689 | 4/1972 | Sapy et al. . |
| 3,659,880 | 5/1972 | Goldsobel . |
| 3,684,319 | 8/1972 | Samartina . |
| 3,698,088 | 10/1972 | Austin . |
| 3,730,564 | 5/1973 | Bachle et al. . |
| 3,749,424 | 7/1973 | Greene . |
| 3,756,632 | 9/1973 | Riggs et al. . |
| 3,874,083 | 4/1975 | Buckley . |
| 3,958,818 | 5/1976 | Mason . |
| 3,973,752 | 8/1976 | Boelkins . |
| 3,980,325 | 9/1976 | Robertson . |
| 3,984,133 | 10/1976 | Bird . |
| 3,990,728 | 11/1976 | Coughlin . |
| 4,005,884 | 2/1977 | Drori . |
| 4,026,025 | 5/1977 | Hunt . |
| 4,032,177 | 6/1977 | Anderson . |
| 4,039,212 | 8/1977 | Skarud . |
| 4,063,760 | 12/1977 | Moreiras . |
| 4,076,279 | 2/1978 | Klotz et al. . |
| 4,109,943 | 8/1978 | Cooke . |
| 4,113,284 | 9/1978 | Blocker . |
| 4,133,564 | 1/1979 | Sarson et al. . |
| 4,138,145 | 2/1979 | Lawrence . |
| 4,149,315 | 4/1979 | Page et al. . |
| 4,157,843 | 6/1979 | Trnka et al. . |
| 4,178,023 | 12/1979 | Guest . |
| 4,187,848 | 2/1980 | Taylor . |
| 4,188,051 | 2/1980 | Burge . |
| 4,193,616 | 3/1980 | Sarson et al. . |
| 4,225,162 | 9/1980 | Dola . |
| 4,229,025 | 10/1980 | Volgstadt et al. . |
| 4,248,589 | 2/1981 | Lewis . |
| 4,249,899 | 2/1981 | Davis . |
| 4,257,629 | 3/1981 | Maple et al. . |
| 4,266,815 | 5/1981 | Cross . |
| 4,275,907 | 6/1981 | Hunt . |
| 4,278,279 | 7/1981 | Zimmerman . |
| 4,293,178 | 10/1981 | Lee . |
| 4,407,526 | 10/1983 | Cicenas . |
| 4,422,673 | 12/1983 | Blackford et al. . |
| 4,445,714 | 5/1984 | Kisiel . |
| 4,451,069 | 5/1984 | Melone . |
| 4,463,974 | 8/1984 | Ergun . |
| 4,481,697 | 11/1984 | Bachle . |
| 4,493,522 | 1/1985 | Law . |
| 4,522,435 | 6/1985 | Miller et al. . |
| 4,564,223 | 1/1986 | Burrington . |
| 4,565,392 | 1/1986 | Vyse . |
| 4,573,716 | 3/1986 | Guest . |
| 4,577,894 | 3/1986 | Wake . |
| 4,613,329 | 9/1986 | Bodicky . |
| 4,619,612 | 10/1986 | Weber et al. . |
| 4,621,842 | 11/1986 | Kowal et al. . |
| 4,637,639 | 1/1987 | Jorgensen et al. . |
| 4,676,749 | 6/1987 | Mabille . |
| 4,679,827 | 7/1987 | Law . |
| 4,705,304 | 11/1987 | Matsuda et al. . |
| 4,712,813 | 12/1987 | Passerell et al. . |
| 4,722,558 | 2/1988 | Badoureaux . |
| 4,750,765 | 6/1988 | Cassidy et al. . |
| 4,787,657 | 11/1988 | Henniger . |
| 4,793,637 | 12/1988 | Laipply et al. . |
| 4,807,911 | 2/1989 | Short . |
| 4,817,997 | 4/1989 | Ingram . |
| 4,826,431 | 5/1989 | Fujimura et al. . |
| 4,842,548 | 6/1989 | Bolante . |
| 4,893,846 | 1/1990 | McGraw . |
| 4,900,068 | 2/1990 | Law . |
| 4,903,995 | 2/1990 | Blenkush et al. . |
| 4,915,427 | 4/1990 | Zahuranec . |
| 4,923,228 | 5/1990 | Laipply . |
| 4,946,200 | 8/1990 | Blenkush et al. . |
| 4,951,976 | 8/1990 | Boelkins . |
| 4,958,858 | 9/1990 | Guest . |
| 4,969,668 | 11/1990 | Sauer . |
| 4,975,054 | 12/1990 | Esrock . |
| 4,984,984 | 1/1991 | Esrock . |
| 5,044,675 | 9/1991 | Sauer . |
| 5,048,872 | 9/1991 | Gehring . |
| 5,049,071 | 9/1991 | Davis et al. . |
| 5,069,424 | 12/1991 | Dennany et al. . |
| 5,125,835 | 6/1992 | Young . |
| 5,176,411 | 1/1993 | DuPont, Jr. . |
| 5,192,206 | 3/1993 | Davis et al. . |
| 5,222,772 | 6/1993 | McGraw . |
| 5,236,356 | 8/1993 | Davis et al. . |
| 5,242,300 | 9/1993 | Esrock . |
| 5,254,103 | 10/1993 | Heuillon . |
| 5,286,065 | 2/1994 | Austin et al. . |
| 5,306,146 | 4/1994 | Davis et al. . |
| 5,320,389 | 6/1994 | Dupont . |
| 5,342,195 | 8/1994 | Davis et al. . |
| 5,370,423 | 12/1994 | Guest . |
| 5,433,485 | 7/1995 | Austin et al. . |
| 5,460,619 | 10/1995 | Esrock . |
| 5,468,027 | 11/1995 | Guest . |
| 5,489,205 | 2/1996 | Davis et al. . |
| 5,507,537 | 4/1996 | Meisinger et al. . |
| 5,591,389 | 1/1997 | Esrock . |
| 5,772,433 | 6/1998 | Esrock . |
| 5,927,975 * | 7/1999 | Esrock ................................. 433/80 |

* cited by examiner

FITTING FOR DENTAL SYRINGE TIP

CROSS-REFERENCE TO RELATED APPLICATION

This is a continuation of application Ser. No. 08/787,243, filed Jan. 24, 1997, now U.S. Pat. No. 5,927,975.

BACKGROUND OF THE INVENTION

This invention relates to air-water syringes, and more specifically to fittings for connecting a syringe tip to a hand-piece of an air-water syringe.

Air-water syringes are used by dentists and dental technicians for many dental procedures, such as cleaning debris from a patient's teeth and mouth. The teeth and mouth are cleaned by spraying a stream of water, air or a combination of water and air from the syringe. A typical air-water syringe has a hand-piece and a syringe tip releasably attached to the hand-piece.

Many dentists use disposable syringe tips to avoid spreading infectious diseases from one patient to another. A typical disposable air-water syringe tip has discrete air and water passageways for communication with air and water passageways of the hand-piece.

Disposable tips are typically received in a connector which is adapted to connect the tip to the hand-piece. The tips are held in place by turning the connector which includes one or more parts which clamp down on the tube. These connectors have a disadvantage in that the tip may not be securely held in the hand-piece if the connector is not adequately screwed onto the hand-piece. This may result in leakage from between the hand-piece and tip or the tip being ejected into the patient's mouth which could result in injury to the patient. Furthermore, the time required to loosen the connector, replace the tip and reattach and tighten the connector is significant considering these steps are repeated several times a day.

Quick-connect type fittings which are presently available eliminate the need for tightening a connector, these fittings, however, require specially formed disposable tips which are expensive to manufacture. These fittings typically include many parts including springs which can wear over time thus increasing the chances of ejecting a tip into a patient's mouth.

Accordingly, there is a need for a quick-connect fitting for connecting a dental syringe tip to a dental syringe hand-piece which is simple to use, reliable and relatively inexpensive to manufacture, and can be used with different types of syringe tips.

SUMMARY OF THE INVENTION

Among the several objects of this invention may be noted the provision of an improved fitting for connecting a syringe tip to a medical syringe which requires only insertion of the tip into the fitting to lock the tip in place; the provision of such a fitting which securely holds the tip in place without tightening a coupling over the tip; the provision of such a fitting which allows for rotation of the syringe tip within the fitting; the provision of such a fitting which is adaptable for use with different types of syringes; and the provision of such a fitting which is economical and easy to manufacture.

Generally, a fitting of this invention is for releasably and sealingly connecting a conduit to a medical instrument. The medical instrument has a socket for receiving the fitting and first and second ports for transfer of first and second fluids to and from the socket. The conduit has a central passageway therethrough for conducting the first fluid and one or more peripheral passageways therethrough for conducting said second fluid. The fitting comprises a body having a proximal end, a distal end and a longitudinal axis extending between the ends. The body has a recess extending on the axis from the distal end toward and terminating short of the proximal end thereof and a bottom adjacent its proximal end. The body is open at its distal end and is formed for attachment to the medical instrument with the proximal end of the body positioned in the socket of the instrument. The fitting further includes first and second passages through the bottom of the body for flow of the first and second fluids respectively. A quick-connect device is mounted in the recess in the body adjacent the distal end of the body for allowing quick connection of the conduit to the body and quick disconnection of the conduit from the body. The quick-connect device has an opening therethrough generally coaxial with the longitudinal axis of the body and comprises a gripping mechanism adjacent the opening. The conduit being receivable within the gripping mechanism for axial movement of the conduit in proximal and distal directions with respect to the body. Movement of the conduit in the proximal direction allows the gripping mechanism to move radially outward relative to the longitudinal axis of the body and movement in the distal direction causes the gripping mechanism to move radially inward toward the longitudinal axis. The gripping mechanism permits one end of the conduit, constituting its proximal end, to be pushed through the opening of the quick connect device to an initial position in the body recess adjacent the bottom of the body. The initial position of the conduit is one in which a tubular connector provides a fluid-tight sealing connection between the central passageway in the conduit and the first passage in the bottom of the body. The gripping mechanism is responsive to a force on the conduit in a distal direction to permit the conduit to move a limited distance away from the bottom of the body. The gripping mechanism is operable to apply a progressively increasing gripping force to the conduit as the conduit moves away from the bottom until the conduit reaches an operating position in which the gripping force prevents substantial further movement of the conduit in a distal direction away from the bottom. The conduit is in its operating position when the proximal end of the conduit is spaced from the bottom of the body to provide a cavity therebetween allowing fluid communication between the second passage in the bottom of the body and the one or more peripheral passageways in the conduit. The tubular connector is adapted to maintain the fluid-tight sealing connection between the first passage in the bottom of the body and the central passageway in the conduit when the conduit is in its operating position. The fitting further includes manually operable means for moving the gripping mechanism in a proximal direction relative to the body to allow the gripping mechanism to move radially outward to release the conduit so it can be removed from the body.

In another aspect of the invention, a medical syringe comprises a hand-piece for transporting first and second fluids between a patient and the syringe. The medical syringe further includes a syringe tip having a central passageway therethrough for conducting the first fluid and one or more peripheral passageways therethrough for conducting the second fluid. The improvement in the medical syringe comprises a tip connector assembly for releasably and sealingly connecting the syringe tip to the hand-piece. The tip connector assembly is similar to the fitting described above.

Generally, a method of the present invention is for connecting a syringe tip to a hand-piece used to transport first and second fluids between a patient and the hand-piece. The syringe tip is of the type having a central passageway therethrough for conducting the first fluid and one or more peripheral passageways therethrough for conducting the second fluid. The hand-piece includes a fitting as described above. The method includes pushing the syringe tip through the opening in the gripping device to an initial position in which the proximal end of the syringe tip is adjacent the bottom of the body and the central passageway in the syringe tip has a fluid-tight sealing connection to the first passage in the bottom of the body. The method further includes moving the syringe tip in a direction away from the bottom of the body thereby causing the gripping mechanism to apply a progressively increasing gripping force to the syringe tip until the syringe tip reaches an operating position in which the gripping force prevents substantial further movement of the syringe tip in a distal direction away from the bottom while maintaining the fluid-tight sealing connection. The operating position of the syringe tip is one in which the proximal end of the syringe tip is spaced from the bottom of the body to provide a cavity therebetween allowing fluid communication between the second passage in the bottom of the body and the one or more peripheral passageways in the syringe tip, and in which the fluid-tight sealing connection between the first passage in the bottom of the body and the central passageway in the syringe tip is maintained.

Another method of this invention is for connecting and disconnecting a disposable syringe tip to and from a hand-piece used to transport first and second fluids between a patient and the hand-piece. The hand-piece has a fitting as described above. The method comprises pushing the proximal end of the syringe tip in a proximal direction into the recess in the body for engagement by the gripping mechanism; applying a force upon the manually operable means in a proximal direction to disengage the syringe tip from the gripping mechanism; and removing the syringe tip from the fitting.

In another aspect of this invention, a connector is used with the fitting described above. The connector comprises a base, a central member extending from the base, and a tubular member extending from one end of the central member and having a generally constant diameter sized for insertion into the central passageway of the syringe tip. The connector is configured such that when the base is positioned between the fitting and the dental syringe the central member extends through the first passage in the body and the tubular member extends into the fluid passageway of the syringe tip. The connector has an opening extending through a central longitudinal axis of the connector for providing fluid communication between the dental syringe and the central passageway of the syringe tip. The connector is releasably and removably attached to the body whereby the connector may be readily replaced.

Other objects and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

Figure 1:
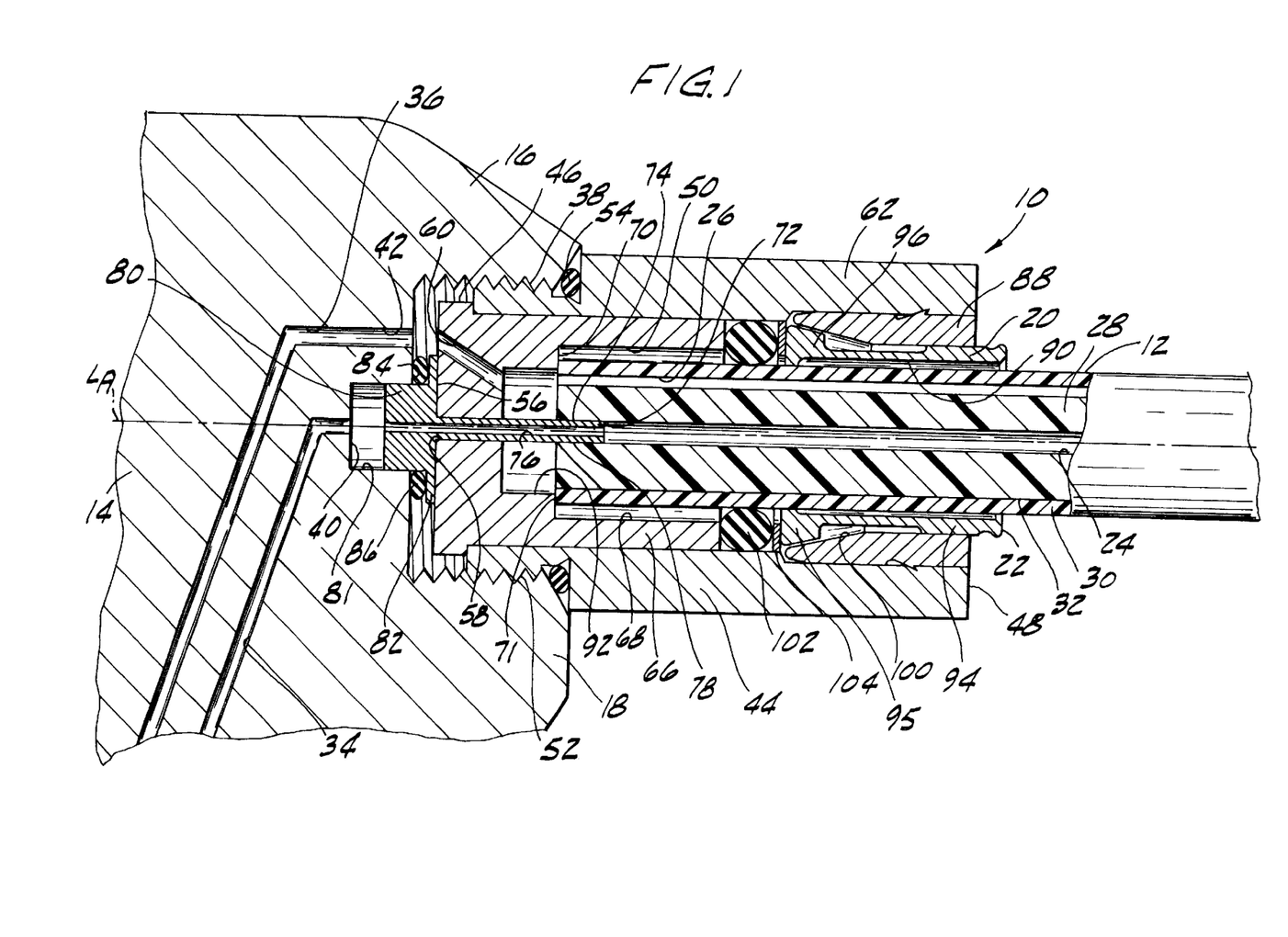
FIG. 1 is a cross-sectional view of a first embodiment of a fitting of the present invention connecting a syringe tip to a dental syringe.

A fitting for connecting a syringe tip 12 to a medical instrument 14 such as an air-water dental syringe is shown in FIG. 1 and generally indicated at 10. The dental syringe 14 delivers air and water to the mouth of a patient and comprises a hand-piece generally indicated at 16. The syringe tip 12 is preferably disposable and is releasably and sealingly engageable with a discharge end 18 of the hand-piece 16. The fitting 10, or connector assembly, is provided for attachment of the syringe tip 12 to the dental syringe 14 for conducting fluids to and from the syringe and the patient. The fitting 10 is a quick-connect fitting which securely holds the tip 12 in place upon pushing the tip into the fitting. The fitting 10 includes a gripping mechanism 20 which prevents removal of the tip 12 from the fitting until a manually operable device 22 is actuated to release the tip from the fitting for easy replacement of the tip.

The syringe tip 12 (conduit) includes a central passageway 24 extending along the length of the tip generally through the center of the tip and a plurality of peripheral passageways 26 surrounding the central passageway and extending the length of the tip. The syringe tip 12 comprises a generally resilient and pliable elongate inner tube 28 extending substantially the entire length of the tip and an outer tube 30 which is stiffer than the resilient and pliable material of the inner tube. The outer tube 30 concentrically surrounds the inner tube 28 and has a smooth continuous outer surface. The inner tube 28 may for example have a fluted outer surface with elongate flutes spaced about the circumference of the outer surface. The flutes and the inner surface of the outer tube 30 define elongate air passageways 26 (peripheral passageways) circumferentially disposed about the central fluid passageway 24 and extending substantially the length of the tube. Preferably, the syringe tip 12 has a generally uniform cross section throughout its entire length. Different tip configurations such as the ones shown in U.S. Pat. No. 5,460,619 and U.S. patent application Ser. No. 08/423,994, which are incorporated herein by reference, may also be used with this fitting 10. It is to be understood that the syringe tip 12 may have only one fluid passageway or more than two fluid passageways and may have configurations other than those described above without departing from the scope of this invention.

The hand-piece 16 includes a handle portion (not shown) for grasping the hand-piece, a first fluid (water) passage 34 for directing a stream of water to the discharge end 18 of the hand-piece 16 and a second fluid (air) passage 36 for directing an air stream to the discharge end of the hand-piece. The hand-piece 16 further includes a threaded socket 38 at its discharge end 18 for threadably receiving the fitting 10 and push buttons (not shown) for discharging air, water or a combination of air and water from the hand-piece. The water and air passages 34, 36 extend from pressurized sources (not shown) to first and second ports 40, 42 in the socket.

The fitting 10 comprises an elongate body 44 having a central longitudinal axis $L_A$ extending between a proximal end 46 and a distal end 48, and a recess 50 extending on the axis from the distal end toward and terminating short of the proximal end thereof. The body 44 is generally cylindrical and includes external threads 52 adjacent to the proximal end 46 for threadably engaging internal threads 53 formed on the socket 38 of the hand-piece 16. The body 44 is formed for attachment to the dental syringe 14 with the proximal end 46 of the body positioned in the socket 38 of the syringe. A seal 54 is circumferentially positioned around the body 44 generally adjacent to the threaded portion 52 of the body to prevent leakage of air from between the body and the hand-piece 16.

The proximal end 46 of the body 44 has a bottom 56 having two passages 58, 60 formed therein extending from one side of the bottom adjacent to the hand-piece 16 to the opposite side of the bottom into the recess 50 of the body. The first passage 58 extends generally through the center of the bottom 56 of the body 44 and along the longitudinal axis $L_A$ of the body. The second passage 60 extends at an angle relative to the first passage 58. The distal end 48 of the body 44 is open for receiving the syringe tip 12. The syringe tip 12 is positioned within the recess 50 such that the central passageway 24 in the tip is in communicating relation at is the end of the tip in the recess in the body 44 with the central passage 58 in the bottom 56 of the body and the peripheral passageways 26 in the tip are in communicating relation at the end of the tip in the recess in the body with the second passage 60 in the bottom of the body.

Figure 3:
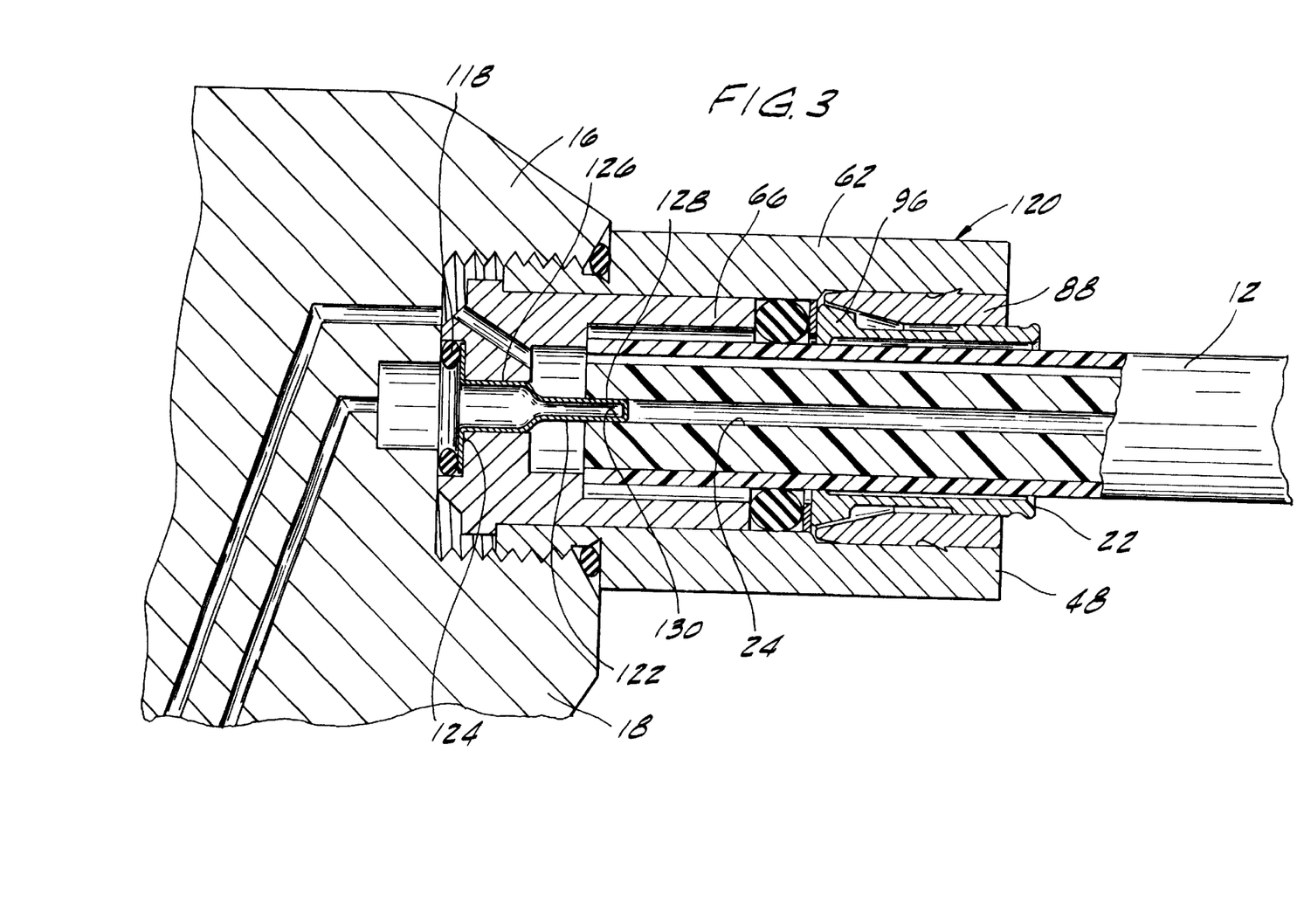
FIG. 3 is a cross-sectional view of a third embodiment of a fitting of the present invention connecting a syringe tip to a dental syringe.

As shown in FIG. 1, the body includes a generally cylindric first body part 62 having a threaded proximal end for threaded attachment to the dental syringe 16. The body 44 further includes a collet 66 which is generally cup-shaped and has a generally cylindric side wall 68 coaxially received inside the proximal end 46 of the first body part 62 and an end wall forming the bottom 56 of the body. The body 44 may also be formed in more than two pieces or as a one piece body as shown in FIG. 3 and described further below. The first body part 62 includes a shoulder 70 formed on the inside wall of the body 44 and spaced longitudinally from the bottom 56 of the body. The shoulder 70 functions as an internal stop for the proximal end 71 of the syringe tip 12 to prevent the tip from contacting the bottom 56 of the body 44 and possibly blocking the second passage 60.

The fitting 10 further includes a connector 72 (tubular connector) having a tubular shaped member 74 which extends from the bottom 56 of the body 44 into the recess 50 and has a bore 76 therethrough forming the first passage 58 of the body. The tubular member 74 has a distal part 78 sized for a sealing fit inside the central passageway 24 of the syringe tip 12 to provide a fluid-tight sealing connection between the central passageway in the tip and the first passage 58 in the bottom 56 of the body 44. The distal part 78 of the tubular member is generally non-tapered and sized for an interference fit inside the central passageway 24. The inner tube 28 is sufficiently pliable to expand radially outward when receiving the tubular member 74 as the syringe tip 12 is pushed toward its initial position and sufficiently resilient to form the fluid-tight sealing connection continuously around the tubular member when fluid flows therethrough. The tubular member 74 is axially slidable within the inner tube 28 as the syringe tip 12 moves along the longitudinal axis $L_A$ of the body 44. The material of the inner tube 28 is sufficiently resilient during the sliding movement to maintain the fluid-tight sealing connection. The tubular member 74 extends from a cylindrical base 80 sized for insertion into a recess 81 in the hand-piece 16. The base 80 includes a flange 82 at its upper end adjacent to the bottom 56 of the body 44. The flange 82 and adjacent surface of the hand-piece 16 form a recess 84 for receiving an O-ring 86 for preventing communication of fluid entering the first passage 58 and fluid entering the second passage 60. The tubular connector 72 may have other configurations including those shown in the alternate embodiments and further described below.

A quick-connect device 88 is mounted in the recess 50 in the body 44 adjacent the distal end 48 of the body for allowing quick connection of the syringe tip 12 to the body and quick disconnection of the syringe tip from the body. The quick-connect device 88 has an opening 90 therethrough generally coaxial with the longitudinal axis $L_A$ of the body 44 for insertion of the tip 12 with the tip extending through the quick-connect device toward the bottom 56 of the body. The quick-connect device 88 may be a device such as available from Weatherhead of Toledo, Ohio under model designation number 1161, Norgren of Littleton, Colo. under the model designation 12 008 0200, Legris of Mesa, Ariz. under model designation 3175 04 11, LF3000, or Parker of Otsego, Mich. under model designation 68PL-5/32-2 or PMCEN-5/32, for example. Quick-connect devices other than those listed may also be used.

The gripping mechanism 20 is part of the quick-connect device 88 and permits the proximal end 71 of the syringe tip 12 to be pushed through the opening 90 of the quick-connect device 88 to an initial position in the body recess 50 adjacent the bottom 56 of the body 44. When the syringe tip 12 is in its initial position, the tubular connector 72 provides a fluid-tight sealing connection between the central passageway 24 in the syringe tip 12 and the first passage 58 in the bottom 56 of the body 44. The syringe tip 12 is mounted within the gripping mechanism for axial movement in the proximal and distal directions with respect to the body 44 and permits the syringe tip 12 to move a limited distance away from the bottom 56 of the body 44 and its initial position to an operating position. The gripping mechanism 20 applies a progressively increasing gripping force to the tip 12 as the tip moves away from the bottom 56 until the tip reaches the operating position in which the gripping force prevents substantial further movement of the tip in a distal direction away from the bottom.

The gripping mechanism 20 is responsive to exertion of force on the tip 12 tending to move the tip in the direction toward the distal end 48 of the body 44 to grip the tip and prevent it from moving out from the communicating relationship with the passages 58, 60 in the bottom 56 of the body 44. The force may be a manual force applied by a person grasping the syringe tip 12 and trying to pull it out of the fitting 10 or a force exerted on the tip by air or water pressure from the hand-piece 16 tending to push the syringe tip in the distal direction. The syringe tip 12 is rotatable on a longitudinal axis of the tip while the syringe tip is in its operating position and while the tip is being gripped by the gripping mechanism.

When the syringe tip 12 is in its operating position, the proximal end 71 of the tip is spaced from the bottom 56 of the body 44 to provide a cavity 92 therebetween allowing fluid communication between the second passage 60 in the bottom of the body and the peripheral passageways 26 in the tip. The tubular connector 72 maintains the fluid-tight sealing connection between the first passage 58 in the bottom 56 of the body 44 and the central passageway 24 in the syringe tip 12.

The gripping mechanism 20 includes the manually operable device 22 for moving the gripping mechanism in a proximal direction relative to the body 44 to allow the gripping mechanism to move radially outward to release the syringe tip 12 so that it can be removed from the body and replaced. The manually operable device 22 comprises a sleeve 94 coaxial with the longitudinal axis $L_A$ of the body 44 and mounted for axial sliding movement relative to the body. The sleeve 94 has a proximal end portion 95 in the recess 50 connected to the gripping mechanism 20 and a distal end portion 97 extending distally beyond the distal end 48 of the body 44 so that it is accessible to an operator of the instrument to be pushed in a proximal direction to move the gripping mechanism in a proximal direction and radially outward to release the syringe tip 12.

The gripping mechanism 20 further includes a plurality of grippers 96 extending from the sleeve 94 toward the bottom 56 of the body 44 generally parallel to the longitudinal $L_A$ axis of the body. The grippers 96 are resiliently biased radially outward as the grippers move in the proximal direction. Movement of the gripping mechanism 20 in the proximal direction allows the grippers to move radially outward relative to the longitudinal axis $L_A$ of the body 44 and movement in the distal direction causes the grippers to move radially inward toward the longitudinal axis. It is to be understood that the grippers 96 may be formed as individual fingers, may be integrally formed as a tubular member or have configurations other than the one shown without departing from the scope of this invention.

Figure 8:
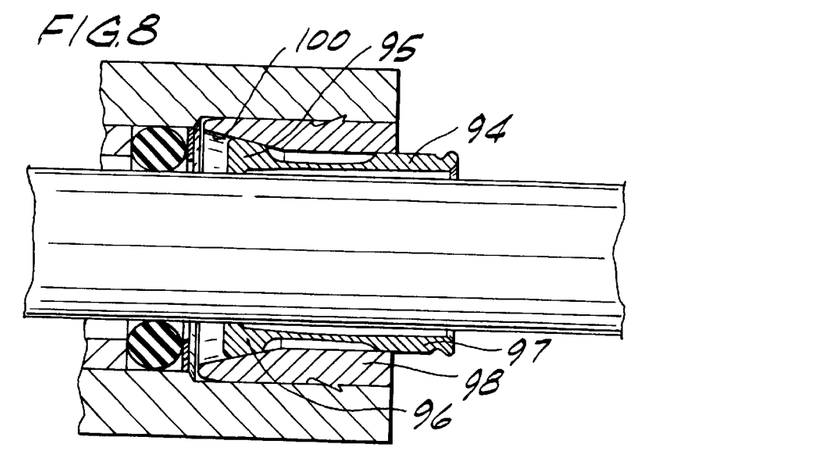
FIG. 8 is a cross-sectional view of a gripping device of the fitting of the present invention, shown in a syringe tip release position.

The quick-connect device 88 includes a tubular insert 98 mounted in the recess 50 surrounding the sleeve 94 and grippers 96. The tubular insert 98 has a camming surface 100 engageable by the grippers 96 to move the grippers radially inward as the grippers move in the distal direction relative to the body 44 to tightly grip the tip 12 (FIG. 8). The tubular insert 98 is press fit into the body 44 but it may also be threaded into the body or held in place by a lock ring or other similar retaining methods. An O-ring 102 is disposed adjacent one end of the collet 66 and a retaining ring 104 holds the O-ring in place. The O-ring prevents leakage of air between the syringe tip 12 and the body 44.

Figure 2:
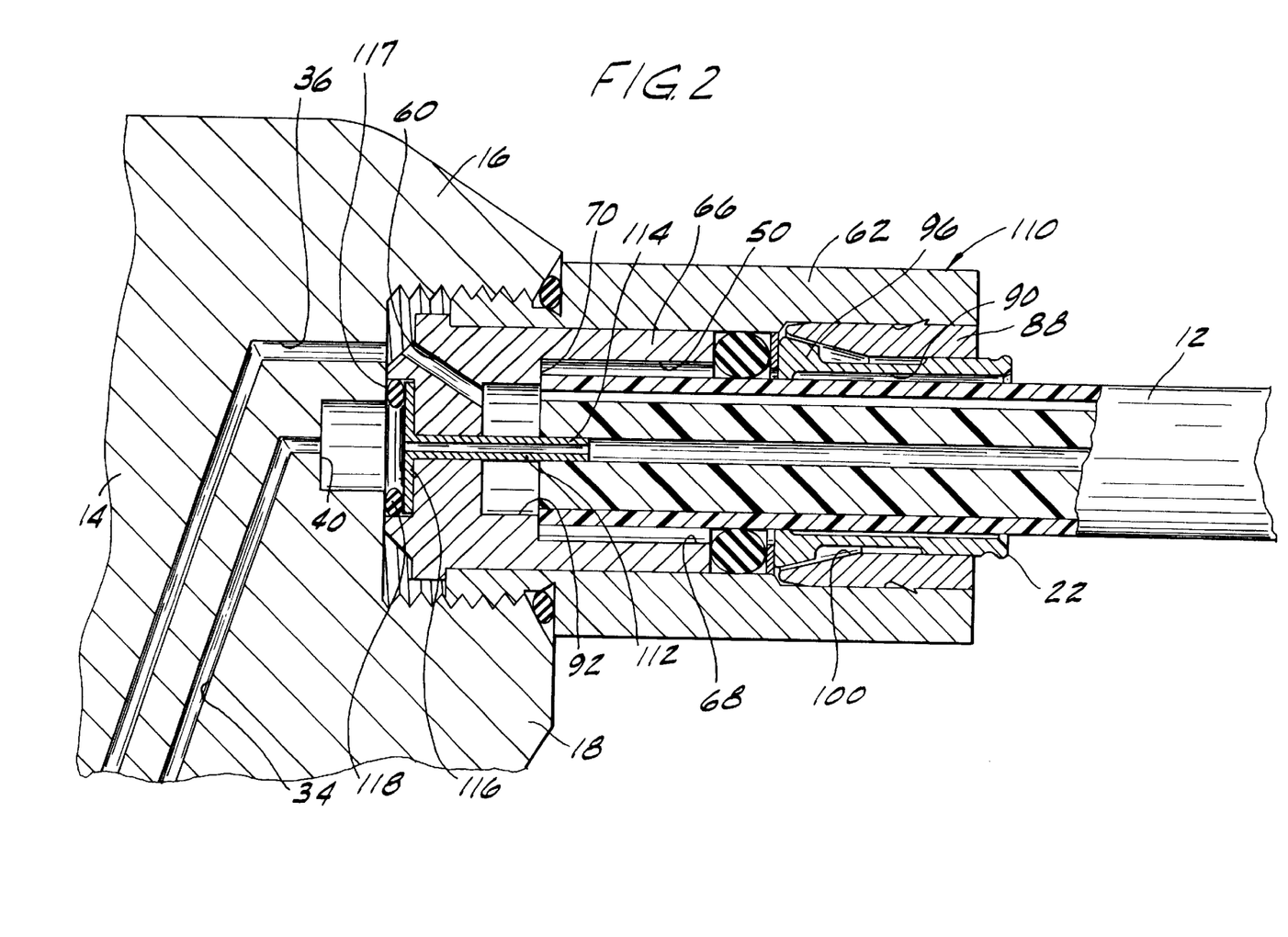
FIG. 2 is a cross-sectional view of a second embodiment of a fitting of the present invention connecting a syringe tip to a dental syringe.

A second embodiment of the fitting of the present invention is shown in FIG. 2 and indicated generally at 110. The fitting 110 is similar to the fitting of the first embodiment but includes a tubular connector 112 having a tubular shaped pin 114 for insertion into the syringe tip 12 and a flange 116 for positioning the pin adjacent to the bottom 56 of the body 44. An O-ring 118 is interposed between the flange 116 and the hand-piece 16. The body includes a recess 117 for receiving the O-ring 118 and flange 116. The flange 116 and O-ring 118 are sized so that the O-ring does not block the second passage 60 in the body 44. The flange 116 is preferably integrally formed with the pin 114.

FIG. 3 shows a third embodiment of the fitting of the present invention 120. The fitting 120 is similar to the fittings 10, 110 shown in FIGS. 1 and 2, except for the tubular connector 122. The tubular connector 122 includes a base 124, a central member 126, and an elongate member 128 extending from one end of the central member. When the base 124 is positioned between the body 44 and the hand-piece 16, the central member 126 extends through the first passage 58 in the body 44 and the elongate member 12 extends into the central fluid passageway 24 of the syringe tip 12. The base 124 has a diameter larger than the first passage in the body so that the connector is retained in the body when the syringe tip is removed from the body. The tubular connector 122 has an opening 130 extending generally along the longitudinal axis $L_A$ of the body 44 for providing fluid communication between the dental syringe 14 and the central passageway 24 of the syringe tip 12. The connector 122 is releasably and removably attached to the body 44 so that the connector may be easily replaced if the opening gets clogged. For example, the base 124 of the tubular connector 122 may have a diameter of 0.120 in., the central member 126 a diameter of 0.069 in. and length of 0.086 in. and the elongate member 128 a diameter of 0.039 in. and a length of 0.124 in. A ratio of the diameter of the elongate member 128 to the central member 126 of the tubular connector 122 described above is in the range of 0.48–0.57. The tip of the elongate member may also be tapered.

Figure 4:
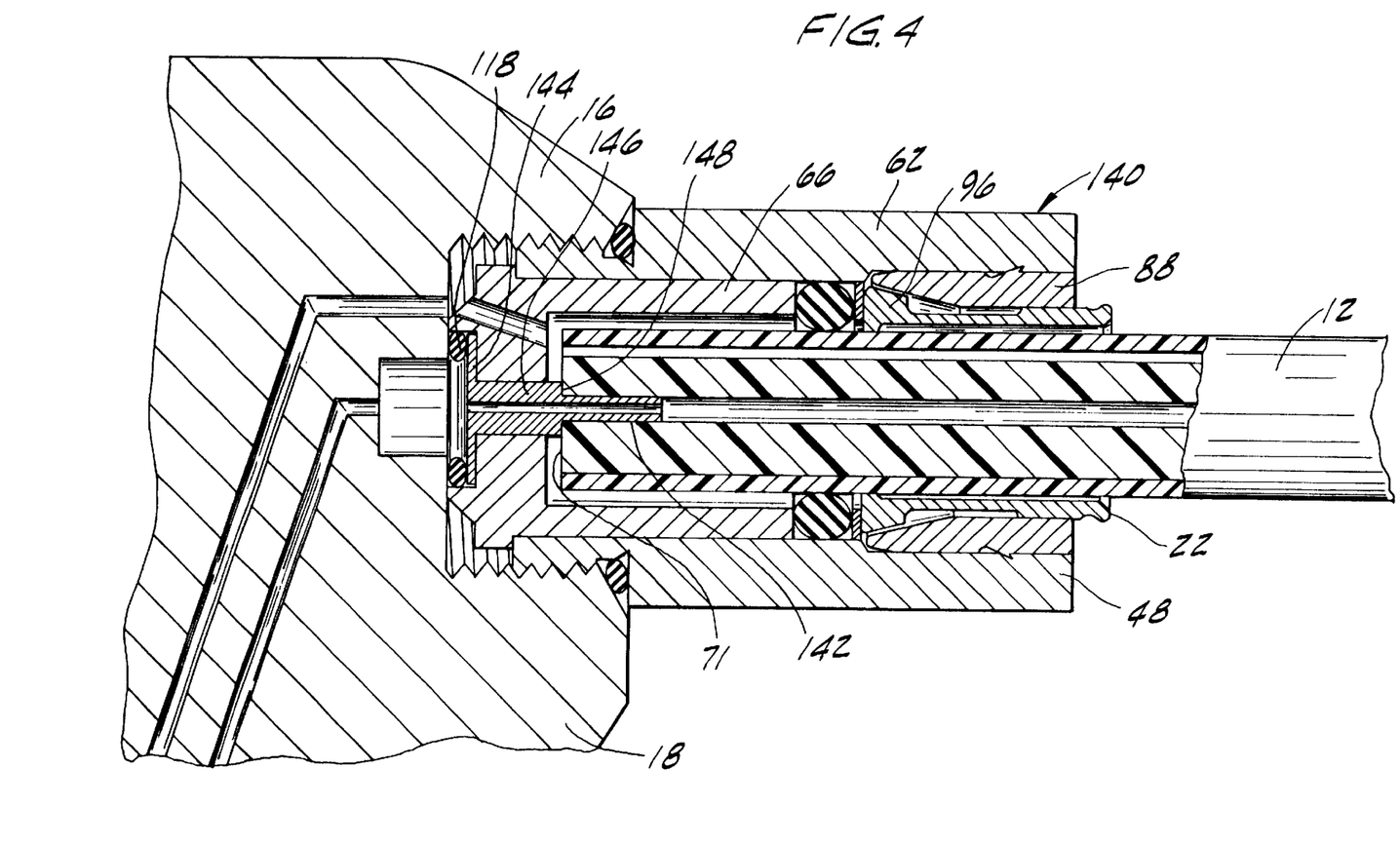
FIG. 4 is a cross-sectional view of a fourth embodiment of a fitting of the present invention connecting a syringe tip to a dental syringe.

FIG. 4 shows a fourth embodiment of the present invention, generally indicated at 140. The configuration of the tubular connector 142 is similar to the tubular connector 122 shown in FIG. 3 except the central member 146 and base 144 have a greater thickness and the central member 146 extends beyond the bottom 56 of the body 44 and into the recess 50 to provide a stop 148 for the syringe tip 12. The body therefore does not require a shoulder for positioning the proximal end 71 of the syringe tip 12.

Figure 5:
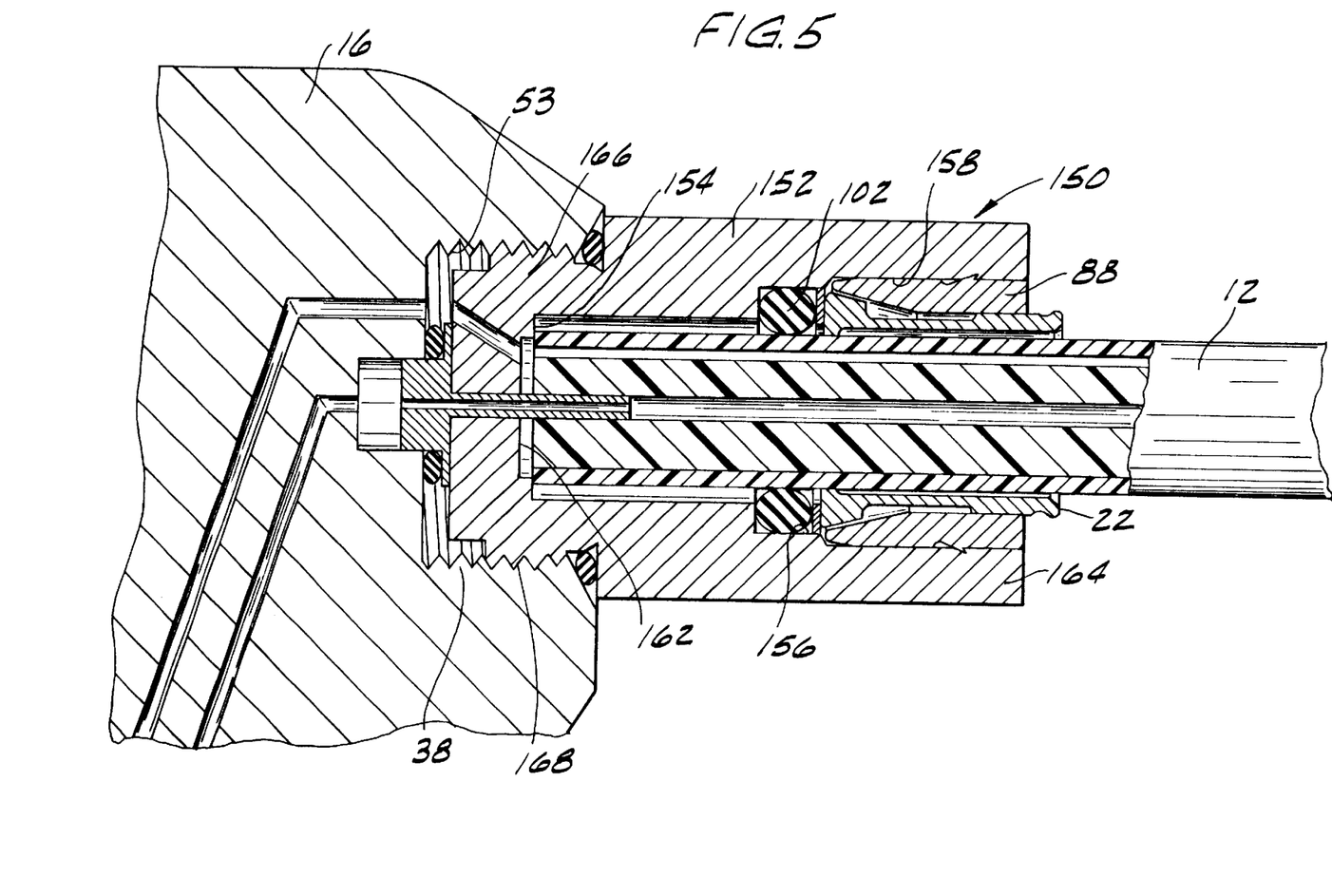
FIG. 5 is a cross-sectional view of a fifth embodiment of a fitting of the present invention connecting a syringe tip to a dental syringe.

A fifth embodiment is shown in FIG. 5 and generally indicated at 150. The fitting 150 includes a body 152 having the collet 66 of the first embodiment integrally formed as one piece with the first body part 62. The body 152 is formed with a shoulder 154 for positioning the tip 12 spaced from the bottom 162 of the body 152. A groove 156 is formed in the body 152 to receive the O-ring 102 for preventing leakage between the tip 12 and the body 152. The opening 168 adjacent the distal end 164 of the body 152 is sized for receiving the quick-connect device 88. The outside diameter of the proximal end 166 of the body 152 includes threads 168 for mating with the internal threads 53 formed in the socket 38 of the hand-piece 16.

Figure 6:
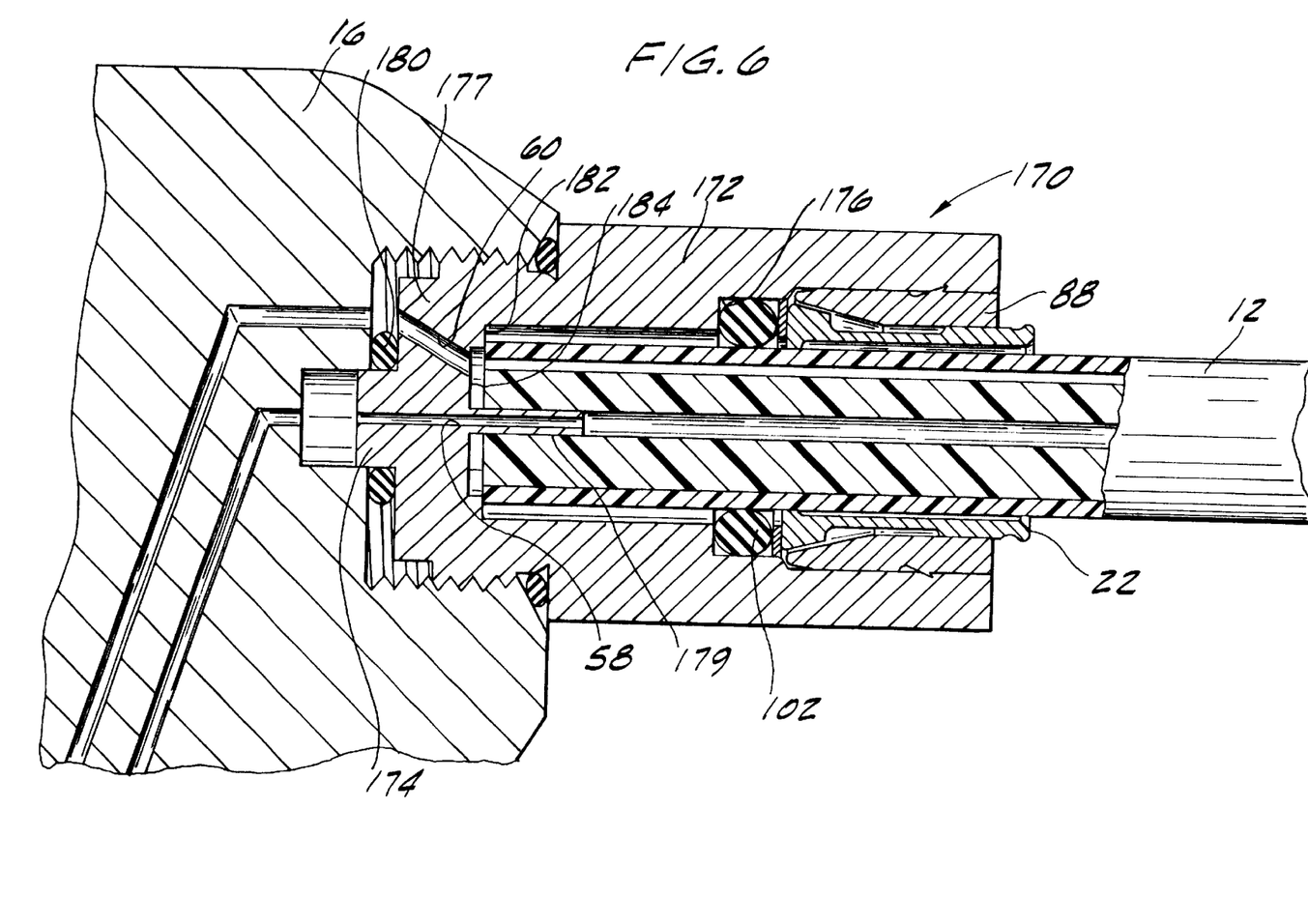
FIG. 6 is a cross-sectional view of a sixth embodiment of a fitting of the present invention connecting a syringe tip to a dental syringe.

A sixth embodiment of the fitting is shown in FIG. 6 and generally indicated at 170. The body and tubular connecter are integrally formed as a one piece body 172.

The passages 58, 60 are formed in the proximal end 177 of the body and the tubular connector 179 constitutes the first passage. The proximal end 177 of the body 172 includes a projection 174 sized for receiving an O-ring 180. The body 172 is formed with a shoulder 182 for positioning the tip 12 spaced from a bottom 184 of the body. A groove 176 is formed in the body 172 to receive the O-ring 102 for preventing leakage between the tip 12 and the body.

Figure 7:
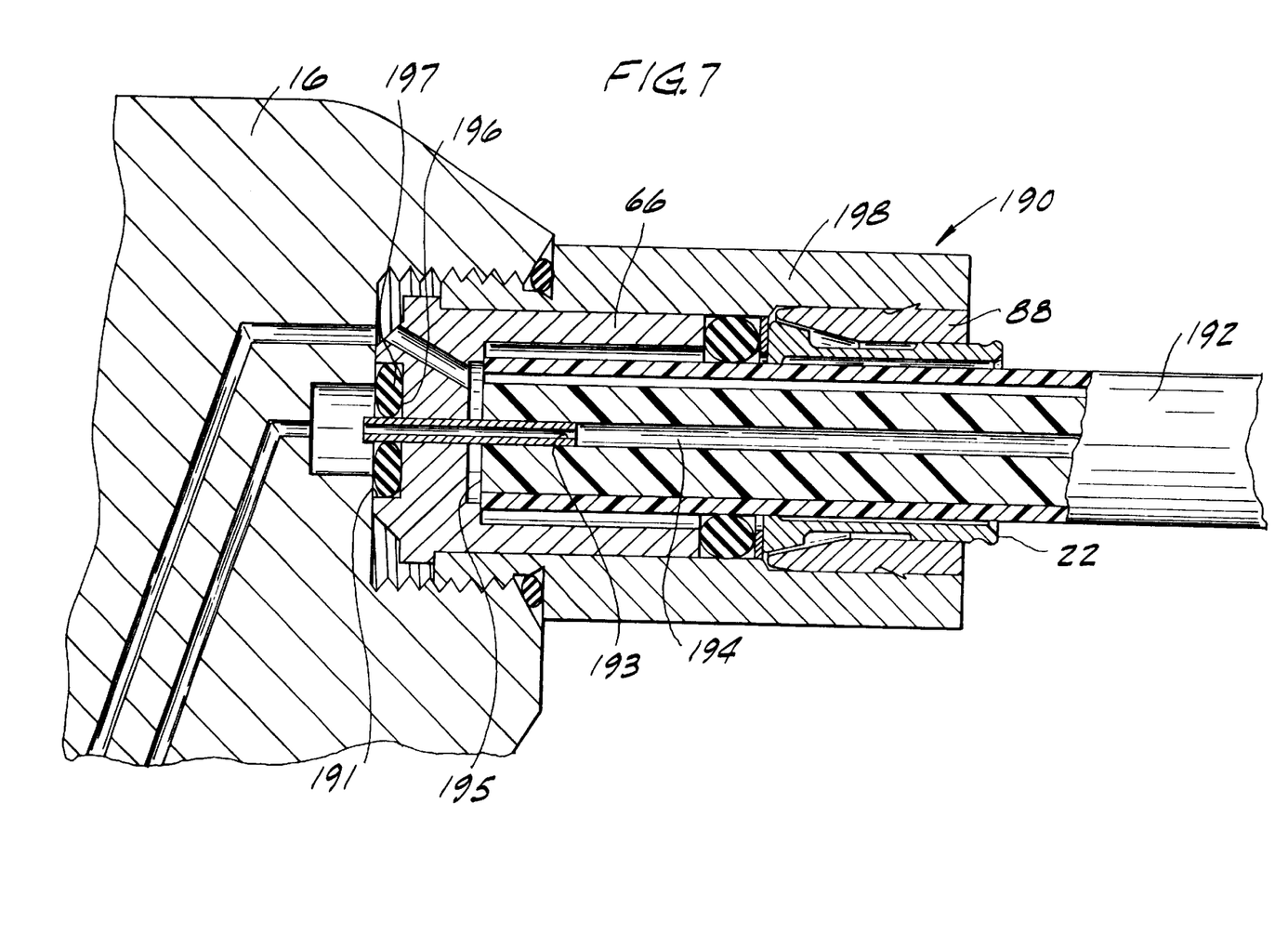
FIG. 7 is a cross-sectional view of a seventh embodiment of a fitting of the present invention connecting a syringe tip to a dental syringe.

A seventh embodiment of the fitting, generally indicated at 190, is shown in FIG. 7. The fitting 190 is configured for receiving a syringe tip 192 having an inner tube 194 extending from the proximal end 195 of the tube. The inner tube 194 forms a central passageway 193 and constitutes the tubular connector. The collet 66 includes a groove 191 for receiving an O-ring 197.

Figure 9:
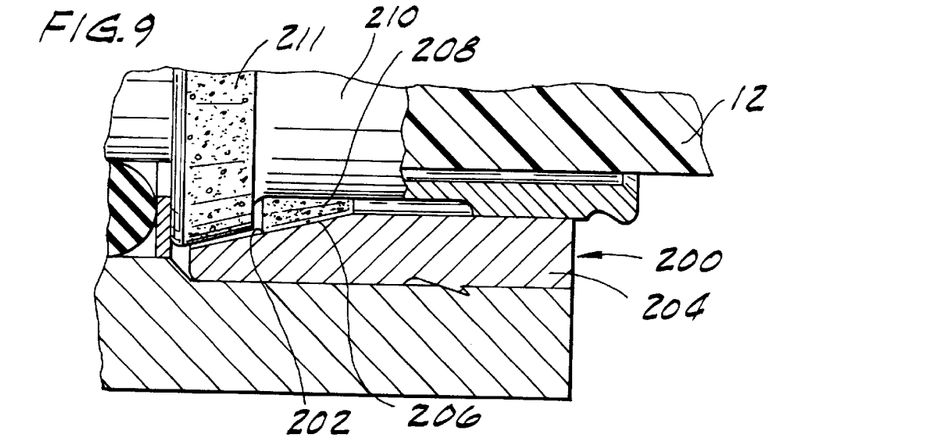
FIG. 9 is a cross-sectional view showing a portion of a gripping device of a seventh embodiment of a fitting of the present invention.
Figure 10:
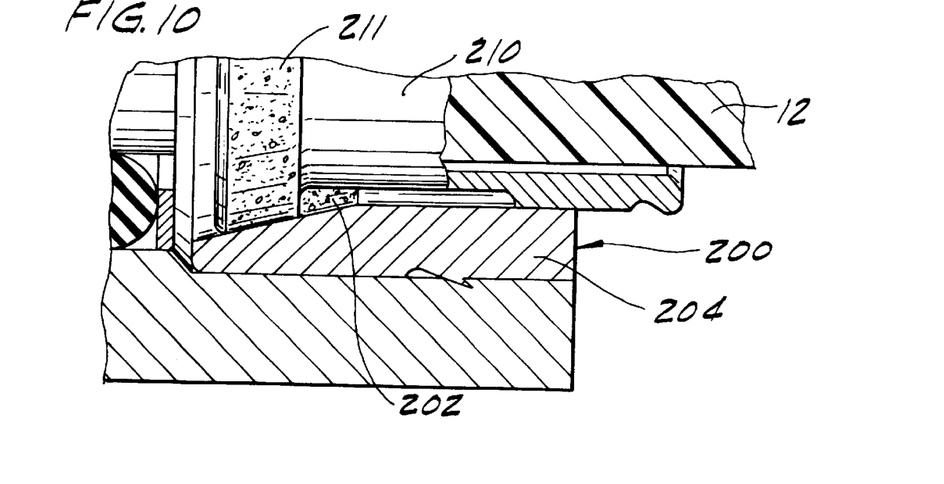
FIG. 10 is a cross-sectional view showing a portion of the gripping device of FIG. 9 in its gripping position.

FIGS. 9 and 10 show a portion of a quick-connect device, generally indicated at 200, of an eighth embodiment of the fitting. The camming surface 202 of the tubular insert 204 comprises a distal portion 206 having a frictionalized surface 208 to prevent rotation of the gripper 210 and syringe tip 12 on a longitudinal axis of the tip when the gripper is engaged with the distal portion of the camming surface when the tip is in its operating position. The grippers 210 also have a frictionalized surface 211 for engagement with the camming surface 202 of the tubular insert 204. It is to be understood that only one of the grippers 210 or distal portion 206 of the camming surface 202 may have a frictionalized surface or the grippers and distal portion of the camming surface may have interlocking surfaces such as splines to prevent rotation of the syringe tip by preventing rotation of the sleeve within the tubular insert when the syringe tip is in its operating position.

In operation, the fitting 10 is threaded into the socket 38 of the hand-piece 16 and the syringe tip 12 is pushed through the opening 90 in the quick-connect device 88 to the initial position in which the proximal end 71 of the syringe tip is adjacent the bottom 56 of the body 44 and the central passageway 24 of the syringe tip has a fluid-tight sealing connection to the first passage 58 in the bottom of the body. The syringe tip 12 is then moved in a direction away from the bottom 56 of the body 44 while maintaining the fluid-tight sealing connection, thereby causing the gripping mechanism 20 to apply a progressively increasing gripping force to the syringe tip until the syringe tip reaches the operating position in which the gripping force prevents substantial further movement of the syringe tip in a distal direction away from the bottom. Any force exerted on the tip 12 to move the tip in the direction toward the distal end 48 of the body 44 will cause the gripping device 20 to tighten the grip of the grippers 96 on the syringe tip. The syringe tip 12 is preferably pulled in the direction toward the distal end 48 of the body 44 to ensure that the tip is securely held in place. The water or air button is then depressed to force air or water from its respective ports 40, 42 in the hand-piece 16 and through the fluid passageways 26, 26 of the syringe tip 12. When the dental procedure has been completed, the syringe tip 12 is removed from the fitting 10 and discarded. In order to remove the tip 12, the manually operable device 22 is pushed in a proximal direction to cause the grippers 96 of the gripping mechanism 20 to move radially outward to release the syringe tip while the tip is pulled out from the body 44.

Although the fitting 10 is described herein as being used for connecting syringe tips 12 to dental syringes 14, it is to be understood that the fitting may be used with other types of dental instruments or various other instruments used in the medical field. For example, the fitting 10 may be used in other dental applications such as for air-abrasive prophylaxis (air polishers), endodontic (root canal) irrigator-aspirators or oral hygiene apparatus. Medical applications for the fitting include ophthalmic surgery irrigator-aspirators, general surgery irrigator-aspirators (lavage), dual lumen catheters and atomizers.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. A fitting for releasably connecting a syringe tip having a longitudinal axis to a dental syringe having a port for supplying a fluid to the syringe tip, the tip having a passageway extending generally parallel to the longitudinal axis for transporting the fluid to a patient's mouth, the fitting comprising:

a body having a connector for attaching the body to the dental syringe and a recess for receiving the syringe tip, the body further having a passage therein extending through the body to the recess;

a quick release mechanism mounted in the recess for quickly connecting the syringe tip to the body and disconnecting the syringe tip from the body, the mechanism including a manually operable actuator moveable in a direction generally parallel to the longitudinal axis between an engaged position in which the quick release mechanism prevents the syringe tip from being removed from the recess and a disengaged position in which the quick release mechanism permits the syringe tip to be removed from the recess; and a tubular connector for extending through the passage into the recess, the tubular connector being sized and shaped for sealingly engaging the passageway of the syringe tip for transporting the fluid from the port of the dental syringe to the syringe tip, said tubular connector having a base with a diameter larger than the passage in the body and adapted to be captured outside the recess in generally fixed position between the body and the dental syringe when the body is attached to the dental syringe so that the base is prevented from passing through the passage into the recess, thereby holding the tubular connector in generally fixed position relative to the body.

2. A fitting as set forth in claim 1 wherein the tubular connector is separable from the body.

3. A fitting as set forth in claim 1 wherein the syringe tip is rotatable about the longitudinal axis while the manually operable actuator is in the engaged position.

4. A fitting for releasably connecting a syringe tip having a longitudinal axis to a dental syringe having a first port for supplying a first fluid to the syringe tip and a second port for supplying a second fluid to the syringe tip, the tip having a first passageway extending generally parallel to the longitudinal axis for transporting said first fluid to a patient's mouth and a second passageway extending generally parallel to the longitudinal axis for transporting said second fluid to the patient's mouth, the fitting comprising:

a body having a connector for attaching the body to the dental syringe, a recess for receiving the syringe tip, a first passage extending through the body to the recess, and a second passage extending through the body to the recess for directing said second fluid from said second port of the dental syringe to said second passageway of the syringe tip;

a quick release mechanism mounted in the recess for quickly connecting the syringe tip to the body and disconnecting the syringe tip from the body, the mechanism including a manually operable actuator moveable in a direction generally parallel to the longitudinal axis between an engaged position in which the quick release mechanism prevents the syringe tip from being removed from the recess and a disengaged position in which the quick release mechanism permits the syringe tip to be removed from the recess; and a tubular connector for extending through the first passage into the recess, the tubular connector being sized and shaped for sealingly engaging said first passageway of the syringe tip for transporting said first fluid from said first port of the dental syringe to the syringe tip, said tubular connector having a base with a diameter larger than the first passage in the body and adapted to be captured outside the recess in generally fixed position between the body and the dental syringe when the body is attached to the dental syringe so that the base is prevented from passing through the first passage into the recess, thereby holding the tubular connector in generally fixed position relative to the body.

5. A fitting as set forth in claim 4 wherein the syringe tip is rotatable about the longitudinal axis while the manually operable actuator is in the engaged position.

6. A fitting for releasably connecting a syringe tip having a longitudinal axis to a dental syringe having a port for supplying a fluid to the syringe tip, the tip having a passageway extending along the longitudinal axis for transporting the fluid to a patient's mouth and further having a substantially constant outer diameter, the fitting comprising:

a body having a connector for attaching the body to the dental syringe and a recess for receiving the syringe tip, the body further having a passage therein extending through the body to the recess; and a quick release mechanism mounted in the recess for quickly connecting the syringe tip to the body and disconnecting the syringe tip from the body, the mechanism including a manually operable actuator adapted to selectively grip the substantially constant outer diameter of the syringe tip to prevent the syringe tip from being removed from the recess; and a tubular connector for extending through the passage into the recess, the tubular connector being sized and shaped for sealingly engaging the passageway of the syringe tip for transporting the fluid from the port of the dental syringe to the syringe tip, said tubular connector having a base with a diameter larger than the passage in the body and adapted to be captured outside the recess in generally fixed position between the body and the dental syringe when the body is attached to the dental syringe so that the base is prevented from passing through the passage into the recess, thereby holding the tubular connector in generally fixed position relative to the body.

7. A fitting as set forth in claim 6 wherein the manually operable actuator comprises a sleeve slidably received in the recess having a plurality of resilient gripping members surrounding the recess, and the quick release mechanism further comprises an angled surface surrounding the gripping members for engaging the gripping members and moving the gripping members radially inward to grip the syringe tip as the sleeve moves away from the dental syringe.

8. A fitting for releasably connecting a syringe tip having a longitudinal axis to a dental syringe having a first port for supplying a first fluid to the syringe tip and a second port for supplying a second fluid to the syringe tip, the tip having a first passageway extending generally parallel to the longitudinal axis for transporting said first fluid to a patient's mouth and a second passageway extending generally parallel to the longitudinal axis for transporting said second fluid to the patient's mouth, the fitting comprising:

a body having a connector for attaching the body to the dental syringe, a recess for receiving the syringe tip, a first passage extending through the body to the recess, and a second passage extending through the body to the recess for directing said second fluid from said second port of the dental syringe to said second passageway of the syringe tip, and a stop in the recess for limiting travel of the syringe tip into the recess;

a quick release mechanism mounted in the recess for quickly connecting the syringe tip to the body and disconnecting the syringe tip from the body, the mechanism being adapted to permit the syringe tip to move away from the stop before gripping the tip sufficiently to prevent farther movement away from the stop; and a tubular connector for extending through the first passage into the recess, the tubular connector being sized and shaped for sealingly engaging said first passageway of the syringe tip when the syringe tip is spaced from the stop for transporting said first fluid from said first port of the dental syringe to the syringe tip, said tubular connector having a base with a diameter larger than the first passage in the body and adapted to be captured outside the recess in generally fixed position between the body and the dental syringe when the body is attached to the dental syringe so that the base is prevented from passing through the opening into the recess, thereby holding the tubular connector in generally fixed position relative to the body.

9. A fitting as set forth in claim 8 wherein the tubular connector slidably engages the first passageway of the syringe tip so that the tubular connector sealingly engages the first passageway when the syringe tip is in contact with the stop and when the syringe tip is spaced away from the stop.

* * * * *